(12) United States Patent
Thanoo et al.

(10) Patent No.: US 8,708,159 B2
(45) Date of Patent: Apr. 29, 2014

(54) MANUFACTURE OF MICROSPHERES USING A HYDROCYCLONE

(75) Inventors: Bagavathikanun Chithambara Thanoo, Brecksville, OH (US); Edward Caldwell Smith, Oakwood Village, OH (US); Mark Smith, Oakwood Village, OH (US)

(73) Assignee: Oakwood Laboratories, LLC, Oakwood Village, OH (US)

( * ) Notice: Subject to any disclaimer, the term of this patent is extended or adjusted under 35 U.S.C. 154(b) by 268 days.

(21) Appl. No.: 13/028,764

(22) Filed: Feb. 16, 2011

(65) Prior Publication Data

US 2012/0205293 A1 Aug. 16, 2012

(51) Int. Cl.
*B04C 5/24* (2006.01)
(52) U.S. Cl.
USPC .......................................... 209/728; 209/712
(58) Field of Classification Search
USPC ........ 209/3, 710–712, 725, 728, 729; 417/54, 417/65
See application file for complete search history.

(56) References Cited

U.S. PATENT DOCUMENTS

| | | | |
|---|---|---|---|
| 4,192,392 A * | 3/1980 | Messines et al. | 175/66 |
| 4,279,743 A * | 7/1981 | Miller | 209/731 |
| 4,810,264 A * | 3/1989 | Dewitz | 48/210 |
| 5,945,126 A | 8/1999 | Thanoo et al. | |
| 6,270,802 B1 | 8/2001 | Thanoo | |
| 6,361,798 B1 | 3/2002 | Thanoo et al. | |
| 6,892,887 B2 * | 5/2005 | Rayborn | 209/17 |
| 6,902,593 B2 * | 6/2005 | Miller et al. | 55/338 |
| 6,939,033 B2 | 9/2005 | Lyons | |
| 7,004,333 B2 * | 2/2006 | Marcotullio et al. | 209/725 |
| 7,300,671 B2 | 11/2007 | Lyons | |
| 7,520,342 B2 * | 4/2009 | Butler et al. | 175/66 |
| 2004/0119179 A1 | 6/2004 | Perrut et al. | |
| 2009/0104274 A1* | 4/2009 | Khopade et al. | 424/490 |
| 2013/0045393 A1* | 2/2013 | Brouns et al. | 428/513 |

FOREIGN PATENT DOCUMENTS

| | | |
|---|---|---|
| KR | 10-2009-0049150 | 5/2009 |
| KR | 10-0924236 B1 | 10/2009 |
| WO | 03092851 | 11/2003 |

\* cited by examiner

*Primary Examiner* — Joseph C Rodriguez
(74) *Attorney, Agent, or Firm* — Pearne & Gordon LLP

(57) ABSTRACT

This disclosure features a system for processing microspheres. A vessel contains a suspension of solidified microspheres comprising polymer and an active agent. A hydrocyclone has a fluid inlet, a first fluid outlet and a second fluid outlet. The fluid inlet is in fluid communication with the vessel and receives the suspension. The second fluid outlet contains a flow of the suspension having concentrated microspheres. The first fluid outlet contains a flow of a relatively large amount of liquid compared to the flow from the second fluid outlet. Also featured is a method of processing the microspheres using the hydrocyclone.

19 Claims, 6 Drawing Sheets

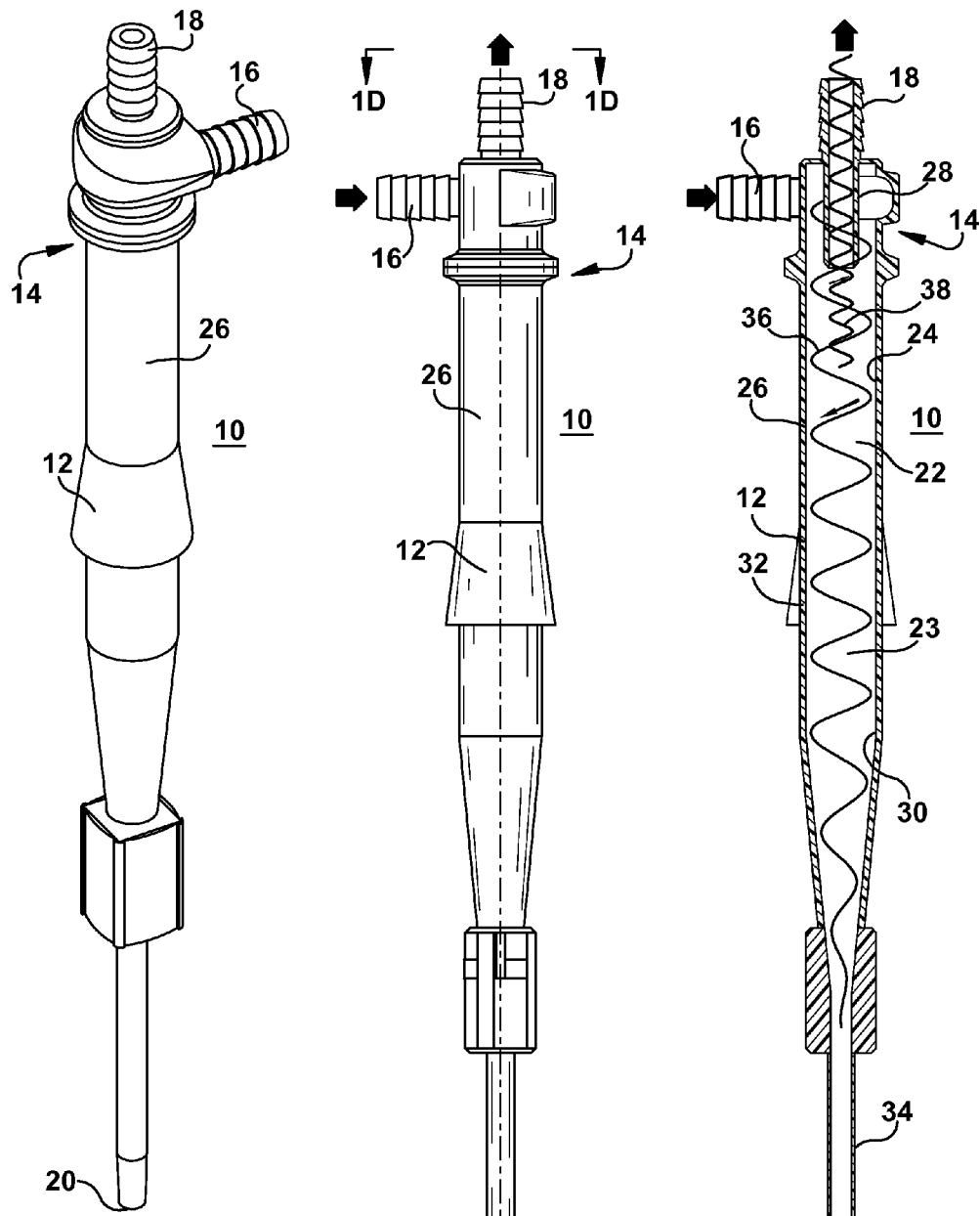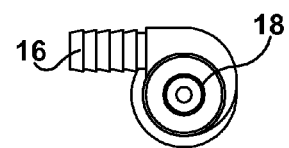

MANUFACTURE OF MICROSPHERES USING A HYDROCYCLONE

TECHNICAL FIELD

The field is the manufacture of sustained release pharmaceutical products.

TECHNICAL BACKGROUND

Sustained release injectable microparticles have attracted attention due to several advantages. They have high patient compliance and convenience due to less frequent injections. Higher efficacy was generally achieved with lower dose due to the maintenance of sustained and effective concentration of the drug in the blood. If necessary, these formulations could be used to achieve higher local concentration to treat specific diseases. However, manufacturing these dosage forms is challenging since the product should be sterile. Standard sterilization methods do not work with these products or adversely affect the quality of the product. Hence the product should be manufactured under aseptic conditions. Aseptic manufacturing of a microparticulate product is challenging. It was established that microparticles could be manufactured by a continuous process as reported in several patents (U.S. Pat. Nos. 5,945,126; 6,270,802; 6,361,798; 7,300,671 and 6,939,033). When making microspheres, it is preferred to produce the particles in a continuous process, such as concentrating the particles to the desired level, removing undesired particles and also removing undesired solvents and surfactants by washing. To produce microparticles in a continuous flow process, equipment is available at various size ranges. For example, in-line dynamic mixers are available at various sizes from manufacturers such as Silverson machines and Ross mixers. Similarly, in-line static mixers are available from companies such as Ross mixers, Sulzer and Komax at various sizes. However, there are not many equipment options to process the microspheres at such a faster rate. Processing involves removing the unwanted components such as excess continuous phase that also contains solvents and non-encapsulated drugs. Equipment such as dead-end filtration (e.g., PharmSep from Swecco, Stir-Cell assembly from Millipore), continuous flow centrifuges (centrifuges from Alfa Lavel) and transmembrane filtration (e.g., hollow fiber filters from GE Healthcare, Spectrum) can process microsphere suspensions. However, dead-end filtration cannot handle large volumes, requires a huge surface area and uses cumbersome equipment with moving parts. Also, clogging of filters and sieves is a common problem during dead end filtration sacrificing the efficiency during the process. For larger scale operations it is necessary to change the clogged filter/sieve and this intervention could affect the aseptic operation. Continuous flow centrifuges may have a problem of particle packing (aggregation) and also are difficult to operate under aseptic conditions. Trans-membrane filtration has a limitation due to the huge surface area requirements and very high flow rate requirement for recirculation. Filter membrane clogging is also a problem for large scale operations. Additionally, removal of small particles from the product becomes necessary in several situations since smaller particles could cause inflammation due to macrophages. Spin filters from Sartorius and vibrating sieves from Swecco are the available options to remove small particles. However, sieve clogging is the major problem for both devices; therefore they are not widely used.

TECHNICAL SUMMARY

A hydrocyclone is used because it is capable of processing large volumes rapidly and can be adapted for aseptic manufacturing. The hydrocyclone occupies minimum space in the aseptic area, does not have any moving parts and can process the microsphere suspension at a faster rate eliminating deficiencies with existing equipment. Additionally, it was found that the hydrocyclone can remove an unwanted fraction of particles that can compromise the quality of the product. While the term microspheres is used throughout this disclosure it is understood that this term is interchangeable with the terms microparticles and microcapsules since the particles may not be strictly spherical and the active agent can be dispersed throughout or encapsulated by the polymer.

Manufacturing of microspheres produces particles with a wide particle size distribution. Smaller particles can pose problems such as initial burst and faster release rate. Small particles may not contain higher drug load compared to larger particles. Additionally, smaller particles may provoke an immune response due to macrophage attack. Therefore, for certain applications it is important that the formulation is free from particles, for example, less than 10 microns, preferably less than 5 microns. As one example, for applications of microparticles to treat osteorarthritis by injecting in synovial tissue, the product should be free from particles less than 20 microns. The hydrocyclone can remove these small particles.

Even though removal of unwanted particle sizes can also be achieved by sieving processes, sieving is difficult under aseptic manufacturing conditions, especially removing a fraction of particles from the product. The hydrocyclone can be used to process the microspheres produced at a faster rate by eliminating the continuous phase at a much faster rate and eliminating smaller particles. This device can also be used to eliminate larger particles. The hydrocyclone can be combined with transmembrane filtration (e.g., a hollow fiber filter) so that the hollow fiber filter can be operated efficiently. Since most of the continuous phase is eliminated by the hydrocyclone it is easy to operate the hollow fiber filter at a lower flow rate (recirculation rate) with simple and smaller pumps such as peristaltic pumps. Additionally, smaller particles that could clog the filter membrane by blocking the pores can be eliminated by the hydrocyclone. By removing a huge fraction of these smaller particles using a hydrocyclone, the operating life of the filter membrane can be extended, thus enhancing the ability to produce large batch sizes. This is useful during aseptic manufacturing since replacing the hollow fiber filter can compromise the asepsis of the process which could lead to rejecting the entire batch.

Similarly, by eliminating a large fraction of smaller particles from the microsphere suspension by hydrocyclone operation the microspheres produced could be processed with less difficulty using dead end filtration (e.g., Swecco sieves). For information about dead end filtration see: AAPS Pharm Sci Tech, 2001, 2(1); US20090104274. If the suspension is substantially free from small particles the processing (concentrating, washing, achieving final formulation) can be performed using the sieve system also.

Microspheres are produced by combining the dispersed phase and continuous phase under the influence of mixing. By selecting the appropriate ratio of the dispersed phase to the continuous phase the output can be a suspension of solidified microspheres or an emulsion. If it is an emulsion, additional fluid can be added to solidify the emulsion by solvent extraction. This could be performed continuously or as a batch process. During the continuous microparticle manufacturing process the suspension output rate can be 1 to 50 L/min depending upon the in-line mixing system. Particle concentration in the suspension can be 0.1 g/L to 100 g/L. Elimination of continuous phase and concentrating microparticles in the suspension are necessary steps during the pharmaceutical preparation. This can be performed by several procedures and associated equipment such as dead-end filtration, centrifugation and trans-membrane filtration, which when used alone have limitations as explained.

In order to increase the rate of microsphere processing while maintaining favorable properties of the microspheres and aseptic nature of the product, the hydrocyclone was found useful. The hydrocyclone significantly increased the process capability and the quality of the microspheres. The hydrocyclone can be easily implemented and used at several different points within the overall process. The hydrocyclone can be used to remove the excess continuous phase (CP) with or without the removal of small particles, to remove larger particles and also during the washing step to remove CP and unwanted components such as residual solvents and non-encapsulated drug.

The hydrocyclone can have an important effect on a sustained release formulation to improve not only its concentration for processing efficiency, but also to help provide formulations which are safer and more effective. The hydrocyclone may be able to help select a preferred particle size distribution in the product. This selection can reduce a fraction that is potentially harmful (or undesirable). Specifically, smaller particles can be reduced or eliminated. These smaller particles can be a potential source of a macrophage attack at the site of injection. The hydrocyclone is capable of processing the microsphere suspension at a much faster rate removing unwanted components compared to other devices.

For fast processing, more than one hydrocyclone can be used in parallel. For good yield more than one hydrocyclone can be used in series. There are several variables in the hydrocyclone that could change the processing efficiency and yield. For a given hydrocyclone different fixed angle apex identifications (IDs) can be selected to manipulate the bottom flow and overflow.

Turning now to a discussion of specific aspects of this disclosure, a first embodiment pertains to a system for processing microspheres comprising a vessel and a hydrocyclone. The vessel contains a suspension of solidified microspheres comprising polymer and active agent. The hydrocyclone has a fluid inlet, a first fluid outlet and a second fluid outlet. The fluid inlet is in fluid communication with the vessel and receives the suspension. The second fluid outlet contains a flow of the suspension having concentrated microspheres. The first fluid outlet contains a flow of a relatively large amount of liquid compared to the flow from the second fluid outlet.

Referring to particular features of the first embodiment, the system can comprise a pump disposed between the vessel and the hydrocylone for pumping the suspension from the vessel to the fluid inlet under pressure. The system can comprise a mixer that combines the polymer, solvent and the active agent to form an emulsion. The mixer is in fluid communication with the vessel and the emulsion is solidified in the vessel to form the suspension in the vessel. Alternatively, the system can comprise another mixer that combines the polymer, solvent and the active agent to form the suspension. The mixer is in fluid communication with the vessel.

A second embodiment of this disclosure features a system for concentrating microspheres comprised of polymer and active agent. The system comprises a mixer and a hydrocyclone. A microsphere suspension could be produced by mixing in the mixer a dispersed phase and a continuous phase. The dispersed phase includes solvent, polymer and an active agent. The mixer includes a mixing element which mixes the dispersed phase and the continuous phase to make a suspension of microspheres. The hydrocyclone has a fluid inlet, a first fluid outlet and a second fluid outlet. The fluid inlet is in fluid communication with the mixer and receives the suspension. The second fluid outlet contains a flow of the suspension having concentrated microspheres and the first fluid outlet contains a flow of a relatively large amount of liquid compared to the flow from the second fluid outlet. Even though the microspheres produced by the mixer could be directly processed by the hydrocyclone, for control purpose it could be performed in two steps with an intermediate vessel receiving the suspension from the mixer and from which a delivery pump will deliver the suspension to the hydrocyclone.

Now, more specific aspects of the second embodiment will be addressed. The system comprises: a vessel for containing and stirring the suspension; first tubing leading from the mixer to the vessel; a source of water or a suspending medium; second tubing leading from the source to the vessel; a pump for moving water or suspending medium from the source along the second tubing into the vessel; third tubing leading from the vessel to the fluid inlet; and a pump for pumping the suspension from the vessel to the fluid inlet The flow from the first fluid outlet can contain a relatively large amount of continuous phase, water or suspending medium as the liquid, compared to the flow from the second fluid outlet.

The flow from the first fluid outlet can contain a relatively large amount of fine microspheres compared to the flow from the second fluid outlet.

The system can also comprise a second hydrocyclone (HC-2) having a fluid inlet, a first fluid outlet and a second fluid outlet. The HC-2 second fluid outlet contains a flow of the suspension having concentrated microspheres and the HC-2 first fluid outlet contains a flow of a relatively large amount of the liquid compared to the flow from the HC-2 second fluid outlet. The first fluid outlet of the hydrocyclone (HC-1) is in fluid communication with the fluid inlet of the second hydrocyclone (HC-2) and the concentrated suspension from the HC-1 second fluid outlet and from the HC-2 second fluid outlet are combined The flow from the first fluid outlet of the second hydrocyclone (HC-2) can contain a relatively large amount of the continuous phase, the water or the suspending medium compared to the flow from the HC-2 second fluid outlet.

The system can comprise a second hydrocyclone in series or parallel with the hydrocyclone.

The system can further comprise a solvent removal vessel (SRV) that receives the combined concentrated suspension from the HC-1 second fluid outlet and from the HC-2 second fluid outlet to achieve washed microspheres with lower residual solvent and free from unwanted components such as surfactant in the CP and non-encapsulated drug.

The system can comprise: a hollow fiber filter (HFF) having a HFF inlet, a first HFF outlet and a second HFF outlet; fourth tubing between the solvent removal vessel (SRV) and the HFF inlet; and a pump for moving the solvent-removed suspension from the SRV, along the fourth tubing to the HFF inlet and fifth tubing extending from the second HFF outlet to the SRV. Permeate is removed from the first HFF outlet, and filtered suspension travels from the second HFF outlet along the fifth tubing to the SRV.

The system can comprise a second source of water or suspending medium, sixth tubing leading from the second source to the solvent removal vessel (SRV) and a pump for pumping the water or the suspending medium from the second source along the sixth tubing into the SRV.

The system can comprise a hollow fiber filter that receives the microsphere suspension traveling from the second fluid outlet of one or more hydrocyclones.

The system can comprise: a wet sieve having a suspension inlet, a liquid outlet and a microsphere outlet; a source of water or suspending medium; tubing leading from the source to the sieve; and a pump for moving the water or the suspending medium from the source along the tubing into the sieve. The suspension inlet of the sieve receives the concentrated suspension from the second fluid outlet of one or more hydrocyclones.

A third embodiment of this disclosure features a method for processing microspheres. A suspension of solidified microspheres comprising polymer and active agent is circulated in a vessel. The suspension is moved from the vessel to a fluid inlet of a hydrocyclone, the hydrocyclone further including a first fluid outlet and a second fluid outlet. A flow of the suspension having concentrated microspheres is removed from the second fluid outlet. A flow of a relatively large amount of a liquid compared to the flow from the second fluid outlet is removed from the first fluid outlet.

Referring to specific aspects of the third embodiment, a pump is disposed between the vessel and the hydrocylone. The pump is used to pump the suspension from the vessel to the fluid inlet under pressure. A mixer can be in fluid communication with the vessel. The polymer, solvent and active agent can be combined in the mixer to form an emulsion. The emulsion can be solidified in the vessel to form the suspension in the vessel. Alternatively, another mixer can be in fluid communication with the vessel. The polymer, solvent and active agent can be combined in the mixer to form the suspension and the suspension can be directed from the mixer to the vessel. The emulsion or suspension can be formed by mixing a dispersed phase comprising polymer, solvent and active agent with a continuous phase. The continuous phase can be aqueous or not.

A fourth embodiment of this disclosure features a method for concentrating microspheres comprised of polymer and active agent comprising: feeding into a mixer a dispersed phase and a continuous phase, the dispersed phase including solvent, polymer and an active agent; mixing the dispersed phase and the continuous phase in the mixer to make a suspension of microspheres; moving the suspension from the mixer to a fluid inlet of a hydrocyclone, the hydrocyclone further including a first fluid outlet and a second fluid outlet; removing from the second fluid outlet a flow of the suspension having concentrated microspheres; and removing from the first fluid outlet a flow of a relatively large amount of a liquid compared to the flow from the second fluid outlet.

Now, specific aspects of the fourth embodiment will be described. The method can comprise: moving the suspension from the mixer to a vessel and stirring the suspension in the vessel; adding water or a suspending medium to the vessel; and moving the suspension from the vessel to the fluid inlet.

The method can comprise removing from the flow from the first fluid outlet a relatively large amount of the continuous phase, the water or the suspending medium.

The method can comprise removing from the flow from the first fluid outlet a relatively large amount of fine microspheres compared to the flow from the second fluid outlet.

The method can comprise providing a second hydrocyclone (HC-2) having a fluid inlet, a first fluid outlet and a second fluid outlet, comprising: moving the suspension from the first fluid outlet of the hydrocyclone (HC-1) to the HC-2 fluid inlet; removing from the HC-2 second fluid outlet a flow of the suspension having concentrated microspheres; removing from the HC-2 first fluid outlet a flow of a relatively large amount of liquid compared to the flow from the HC-2 second fluid outlet; and combining the concentrated suspension from the HC-1 second fluid outlet and from the HC-2 second fluid outlet to form a combined suspension.

The method can comprise removing from the flow from the HC-2 first fluid outlet a relatively large amount of fine microspheres compared to the flow from the HC-2 second fluid outlet.

The method can comprise passing the microsphere suspension from the hydrocyclone to a second hydrocyclone in series or parallel with the hydrocyclone.

The method can comprise passing the flow of the microsphere suspension from the second fluid outlet of the hydrocyclone to a hollow fiber filter.

The method can comprise providing a solvent removal vessel (SRV); moving the combined suspension into the SRV; and removing solvent from the combined suspension in the SRV to form a solvent-removed suspension.

The method can comprise adding water or a suspending medium into the solvent removal vessel (SRV).

The method can comprise: providing a hollow fiber filter (HFF) to remove solvent from the combined suspension in the SRV, the HFF including a HFF inlet, a first HFF outlet and a second HFF outlet; moving the solvent-removed suspension from the solvent removal vessel (SRV) to the HFF inlet; removing water or the suspending medium from the first HFF outlet to form a filtered suspension, and moving the filtered suspension from the second HFF outlet to the SRV.

The method can comprise: providing a wet sieve including a suspension inlet, a liquid outlet and a microsphere outlet; adding water or a suspending medium to the sieve. The suspension inlet of the sieve receives the concentrated suspension. The microspheres are removed from the microsphere outlet of the sieve and the liquid is removed from the liquid outlet.

Many additional features, advantages and a fuller understanding of the invention will be had from the accompanying drawings and the detailed description that follows. It should be understood that the above Technical Summary provides a description in broad terms while the following Detailed Description provides a more narrow description and presents embodiments that should not be construed as necessary limitations of the broad invention as defined in the claims.

BRIEF DESCRIPTION OF THE DRAWINGS

FIG. 1A is a perspective view of a hydrocyclone; FIG. 1B is a side view of the hydrocyclone; FIG. 1C is a vertical cross-sectional view of the hydrocyclone of FIG. 1B and FIG. 1D is a top view of the hydrocyclone as seen along 1D-1D of FIG. 1B;

DETAILED DESCRIPTION

Figure 2:
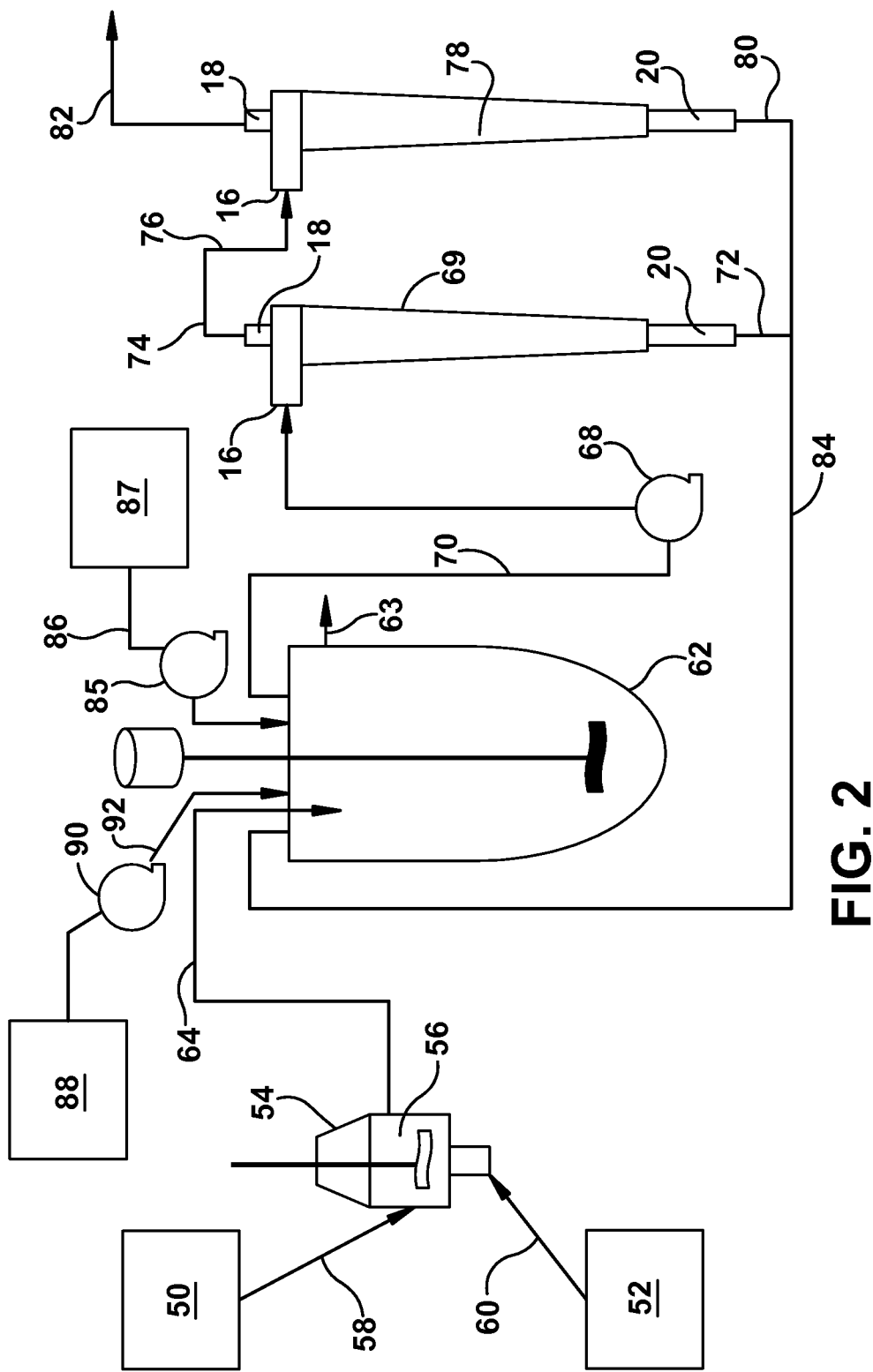
FIG. 2 is a flow diagram for an improved pharmaceutical production process of sustained release microspheres with a hydrocyclone to remove continuous phase (CP), wash microspheres, and formulate in a suspending medium to prepare a final dosage form.

Referring to FIG. 1, a hydrocyclone 10 includes a body 12 having a top portion 14 including a fixed inlet 16, a fixed overflow outlet 18 and a fixed underflow outlet 20. The hydrocyclone is tubular so that the interior 22 of the hydrocyclone is hollow. The hydrocyclone has a center space 23 surrounded by interior walls 24 of the hydrocyclone. The hydrocyclone is in the form of a cylinder having a straight section 26 where the walls on the exterior are the same diameter throughout the middle portion of the hydrocyclone. The top portion includes a straight section portion or a vortex finder 28 extending from the interior to the overflow outlet 18. The interior of the hydrocyclone also includes an angled bore 30 which slopes from the straight section at the middle portion 32 of the hydrocyclone to a decreasing diameter near a bottom portion 34 of the hydrocyclone. The interior surface of the angled bore leads to the outside of the hydrocyclone at the underflow outlet. The vortex 36 receives a flow of material from the outside via inlet 16 under pressure (i.e, under positive pressure such as 10 psi, wherein the actual pressure for operation would be optimized). The release of the material against the angled bore 30 separates the flow of material into two different pathways towards the top portion 14 and bottom portion 34 of the hydrocyclone. Heavier or larger particles travel downward and outward along the main vortex 36 in the interior and leave through the underflow outlet 20. A small proportion of lighter or finer particles travel upward along a center of the main vortex at 38 and leave the interior of the hydrocyclone near its top portion through the overflow outlet 18. A majority of the fluid in the hydrocyclone leaves through the overflow outlet. This fluid may include water, continuous phase or diluents or a combination thereof.

FIG. 2 shows a process flow diagram of the improved method for processing a microsphere suspension using hydrocyclones. The microsphere suspension is processed by removing the continuous phase (CP) along with solvents and non-encapsulated drug, washing the microspheres with water and also suspending the washed microspheres with an appropriate formulation solution. In the flow chart, 50 is a continuous phase (CP) source and 52 is a dispersed phase (DP) source. A mixer 54 produces a microsphere suspension 56 from the DP and CP. Tubing 58, 60 permits flow of the CP and DP from the sources of CP and DP into the mixer. It should be appreciated that the tubing entry locations into the mixer and locations relative to the other devices of the systems of this disclosure are only schematic and can be different in actual practice. The microsphere suspension 56 from the mixer enters a solvent removal vessel 62 (SRV). Tubing 64 permits travel of the microsphere suspension 56 from the mixer 54 to the solvent removal vessel 62. For the delivery of CP and DP appropriate delivery pumps or devices are used (not shown).

The suspension in the vessel is delivered by a pump 68 to the hydrocyclone 69. The pump 68 is located along tubing 70 from the solvent removal vessel 62 to the inlet 16 of the hydrocyclone 69. Depending upon the extent of CP removal from the suspension and also the removal of small particles from the system, more than one hydrocyclone could be used. The flow chart describes the use of two hydrocyclones in series. The underflow 72 from the underflow outlet 20 is a concentrated suspension of microspheres and the overflow 74 from the overflow outlet 18 is mainly continuous phase CP with a small amount of smaller microspheres. Tubing 76 extends from the overflow outlet 18 of the first hydrocyclone 69 to the inlet 16 of a second hydrocyclone 78. The overflow 74 is further delivered along tubing 76 into the inlet port 16 of the second hydrocyclone 78 ("HC-II"). No additional pump is necessary for this delivery. If necessary, pressure gauges could be introduced at the inlet ports to monitor the flow for process control and monitoring purposes. From the second hydrocyclone 78 (HC-II) the concentrated suspension will flow as underflow 80 from the underflow outlet 20 and overflow 82 will leave through the overflow outlet 18 as a waste stream. Additional hydrocyclones could be used in series or in parallel for processing aids.

Tubing 84 extends from the underflow outlets 20 of the hydrocyclones 62 and 78 into the solvent removal vessel 62. Under-flows 72 and 80 are concentrated suspensions that are combined and travel along the tubing 84 to reach back into the solvent removal vessel 62 (SRV). A pump 85 extends along tubing 86 from a wash water reservoir 87 to the solvent removal vessel 62. Washing water from the wash water reservoir 87 can be pumped along the tubing 86 into the SRV 62 using pump 85. For some processes, water is also added simultaneously with the microsphere suspension during the microsphere formation step. The inlet from the Silverson mixer can be closed to enable the concentration of HC treated microspheres to increase and continuous phase to decrease. This operation is for the situation in which the hydrocyclone is used for removing excess CP and smaller microspheres, the microspheres are washed with water and then performing diluent exchange. At the end, the suspension of microspheres in diluent in tank 62 is ready to fill into vials and freeze dry, or ready for bulk freeze drying and can leave via the outlet 63.

There are certain flow rate requirements to perform the entire operation in a confined space so that the volume does not outgrow in the SRV 62. In general, the combined flow rate of the microsphere suspension along tubing 64 and wash water along tubing 86 should be similar to flow rate of overflow through 82. Even though the flow rate mentioned above is desirable, it is not necessary when the capacity of the SRV 62 is sufficiently large and capable of accommodating the increasing volume. During the microsphere washing step there will not be any flow through 64. At this point the flow rate through 86 should be equal to 82.

After washing the microspheres with water, appropriate diluent (suspending medium) can be introduced instead of water. 88 is a diluent reservoir and 90 is a diluent input pump. The diluent pump 90 extends along tubing 92 from the diluent reservoir 88 to the solvent removal vessel 62. The diluent is pumped using pump 90 from the diluent reservoir 88 along the tubing 92 to the SRV 62. Performing this operation will suspend the microspheres in an appropriate suspending medium. Again, flow rate through 92 should be matched to 82 to maintain constant volume in the SRV. The concentration of the microspheres can be increased by continuing the hydrocyclone operation without input into the SRV through the stream along tubing 64, or decreased by not performing the hydrocyclone treatment (i.e., not pumping using pump 68) while adding diluents through the stream along tubing 92. This process will allow the achievement of final formulation with appropriate potency of the drug. The suspension can be further filled into vials and freeze dried. The suspension can also be freeze dried directly to achieve the product as a bulk powder. Filling is carried out aseptically by a standard procedure adopted by the industry. The filling machine is automated; vials will be open to laminar flow of HEPA filtered air and the procedure is qualified by media fill.

The diluent components of this disclosure may include a viscosity enhancer, a small molecule solute as a lyoprotecting agent, and a surfactant. The viscosity enhancer is a water soluble polymer that helps to suspend the particles and slows the particle settling if not mixed.

Suitable viscosity enhancing polymers are carboxy methyl cellulose (CMC), hydroxy propyl cellulose (HPC), hydroxy propyl methyl cellulose (HPMC), sodium carboxy methyl cellulose (SCMC), ethyl cellulose, hydroxy methyl cellulose, cellulose acetate phthalate, hydroxy methyl cellulose acetate succinate, maleic anhydride copolymer, hyalauronic acid, gelatin, high molecular weight polyethylene glycol, and combinations thereof. In one embodiment, carboxy methyl cellulose (CMC) may be used as a viscosity booster as part of the diluent formulation.

The lyoprotecting agent is a small molecule solute, for example, mannitol, sorbitol, sucrose, lactose, galactose, maltose, trehalose, dextrose, fructose, other sugar derivatives, cyclodextrins, and mixtures thereof. Polysaccharides such as starch, dextran, agar, xanthan, and mixtures thereof may be used. Stabilizers such as polyvinyl alcohol, polyvinyl pyrrolidone (PVP), polyethylene glycol (PEG), polyglutamic acid, and mixtures thereof may be used. The cryoprotecting agent may also be used to adjust the tonicity of the solution. In a first embodiment, mannitol is used as the lyoprotecting agent. The lyoprotecting agent may also be helpful to protect the isotonicity of the suspension for injectability.

The surfactant is a wetting agent that is selected from a group of biocompatible surfactants. Polysorbate 80 can be used in one embodiment. Other suitable surfactants include sodium cholate, sodium taurocholate, sodium taurodesoxycholate, lecithin, phospholipids, poloxamers, sorbitan esters, esters of fatty acids with polyoxyalkylene glycols, glycerolpolyalkylene stearate, homo- and copolymers of polyalkylene glycols, Pluronic F68, Tween 20, Tween 40, Tween 80, Span 20, Span 40, Span 60, Span 80, HCO-50, HCO-60 emulsifiers such as gelatin, low molecular weight alcohols such as propylene glycol, and low molecular weight fatty acids.

Diluent could be sterile filtered to use in the formulation. The composition is processed as a suspension and is substantially free from aggregation. The suspended microspheres are easily freeze dried and compatible with agents added. The composition is also found to have reduced water content providing greater stability for long term storage.

FIG. 3 shows a process flow diagram in which a microsphere suspension is received in an intermediate vessel (IMV), processed by a hydrocyclone for concentrating microspheres by removing the continuous phase (CP) and subsequently processing the suspension by a hollow fiber filter (HFF) into a solvent removal vessel (SRV). In FIG. 3, 100 is a source of the continuous phase (CP) and 102 is a source of the dispersed phase (DP). A mixer 104 produces a microsphere suspension 106 by mixing the DP and the CP. Suitable mixers are disclosed in U.S. Pat. No. 5,945,126, which is incorporated herein by reference. Tubing 108 extends from the source of the continuous phase 100 into the mixer 104 and tubing 110 extends from the source of the dispersed phase 102 into the mixer. Tubing 112 extends from the mixer to an intermediate vessel (IMV) 114. The microsphere suspension from the mixer travels along the tubing 112 and enters the intermediate vessel (IMV) 114. It may be possible to pass the suspension coming out of the Silverson mixer directly to the hydrocyclone only if the suspension coming out of the mixer has sufficient positive pressure. Instead, it is easier to receive in an intermediate vessel and control the pressure using pump 116. This will provide good flexibility. For the delivery of CP and DP appropriate delivery pumps or devices may be used (not shown).

The microsphere suspension in the intermediate vessel (IMV) is delivered by a pump 116 into the inlet of a first hydrocyclone (HC-1) 120. The pump 116 is located along tubing 118 that extends from the intermediate vessel to the inlet 16 of the first hydrocyclone 120. Depending upon the extent of CP removal from the suspension and the removal of small particles from the system, more than one hydrocyclone can be used. The flow chart describes the use of two hydrocyclones in series. However, the process is not limited to two hydrocyclones. Underflow 122 from the underflow outlet 20 of the first hydrocyclone 120 is a concentrated suspension of microspheres and overflow 124 from the overflow outlet 18 of the first hydrocyclone is mainly a relatively large volume of CP with a small amount of smaller microspheres. Tubing 126 extends from the overflow outlet 18 of the first hydrocyclone 120 to the inlet 16 of a second hydrocyclone 128. The overflow 124 is further delivered along the tubing 126 into the inlet 16 of the second hydrocyclone 128 (HC-2). No additional pump is necessary for this delivery. If necessary, pressure gauges could be introduced at the inlets to monitor the flow for process control and monitoring purposes. From the second hydrocyclone (HC-2) 128, the concentrated suspension will flow as underflow 130 from the underflow outlet 20 and overflow 132 leaves the overflow outlet 18 as a waste stream.

Tubing 134 extends from the underflow outlets 20 of the first and second hydrocyclones 120, 128 to a solvent removal vessel (SRV) 136. The underflow 122, 130 from the hydrocyclones HC-1 120 and HC-2 128 (concentrated suspension) is combined and travels to the SRV 136 along tubing 134. From the SRV, the suspension is re-circulated using a pump 138 through a hollow fiber filter (HFF) 140. The hollow fiber filter includes a body 142 having an inlet port 144, a permeate removal port 146 and an outlet port 148. The pump 138 is disposed along tubing 150 that extends from the solvent removal vessel SRV to the inlet 144 of the hollow fiber filter HFF. While the suspension is re-circulating through the HFF loop, permeate is removed through the port 146. A pump 152 can be used to remove the permeate. The removal rate of permeate can be matched to the under flow from the hydrocyclones to maintain the volume level in the SRV. It is not necessary to match the flow, if the SRV volume allows. Tubing 153 extends from the outlet 148 of the hollow fiber filter to the SRV 136. The microsphere suspension having permeate (e.g., continuous phase, water or diluent) removed travels from the hollow fiber filter along the tubing 153 into the SRV.

Tubing 156 extends from a wash water source 154 to the intermediate vessel 114 and tubing 158 extends from the wash water source 154 to the solvent removal vessel 136. A pump 159 extends along the tubing 156, 158. After the microsphere formation step is completed, the microspheres in the SRV 136 can be washed with water that travels from the water source 154 along the tubing 158 into the SRV. Water can be added to the microsphere suspension in the IMV 114 also if the process requires immediate water dilution during microsphere formation. The water would travel from the water source 154 along the tubing 156 and to the intermediate vessel 114. A pump 162 is located along tubing 164 that extends from the diluent storage vessel 160 to the solvent removal vessel 136. Microspheres can be recovered from the SRV 136 via outlet 137 as a bulk and dried or they can be suspended in appropriate formulating agent (diluent) pumped from diluent storage vessel 160 along tubing 164. Suspending the microspheres in diluents could be performed in the SRV itself or in another vessel using another HFF. The microsphere suspension in water or in diluents removed from the SRV via outlet 137 could be filled in vials and freeze dried by the standard techniques.

Figure 3:
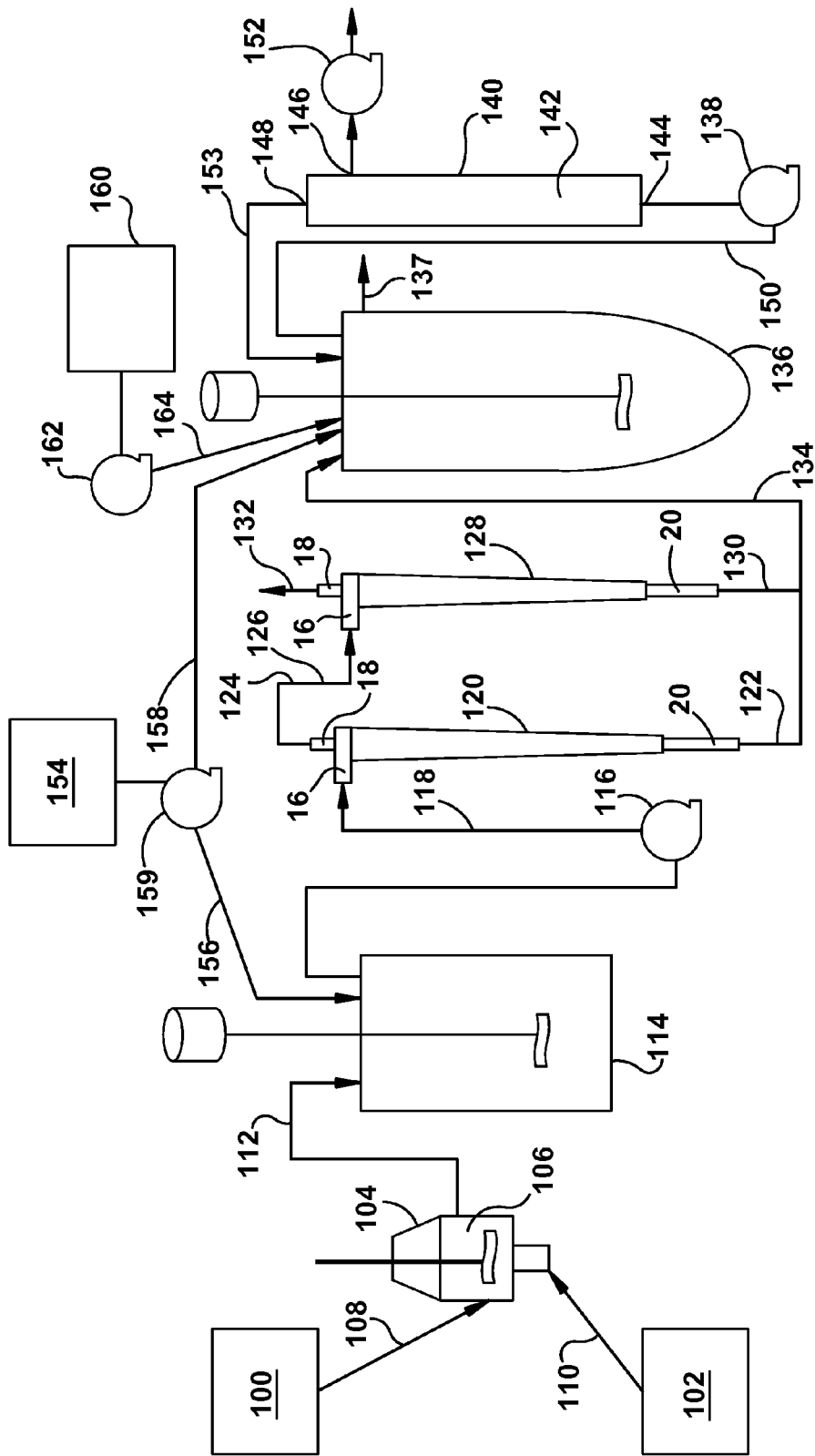
FIG. 3 is a process flow diagram of an improved pharmaceutical production process of sustained release microspheres with the hydrocyclone in use along with a hollow fiber filter to remove CP, wash microspheres, and formulate in a suspending medium to prepare a final dosage form.
Figure 4:
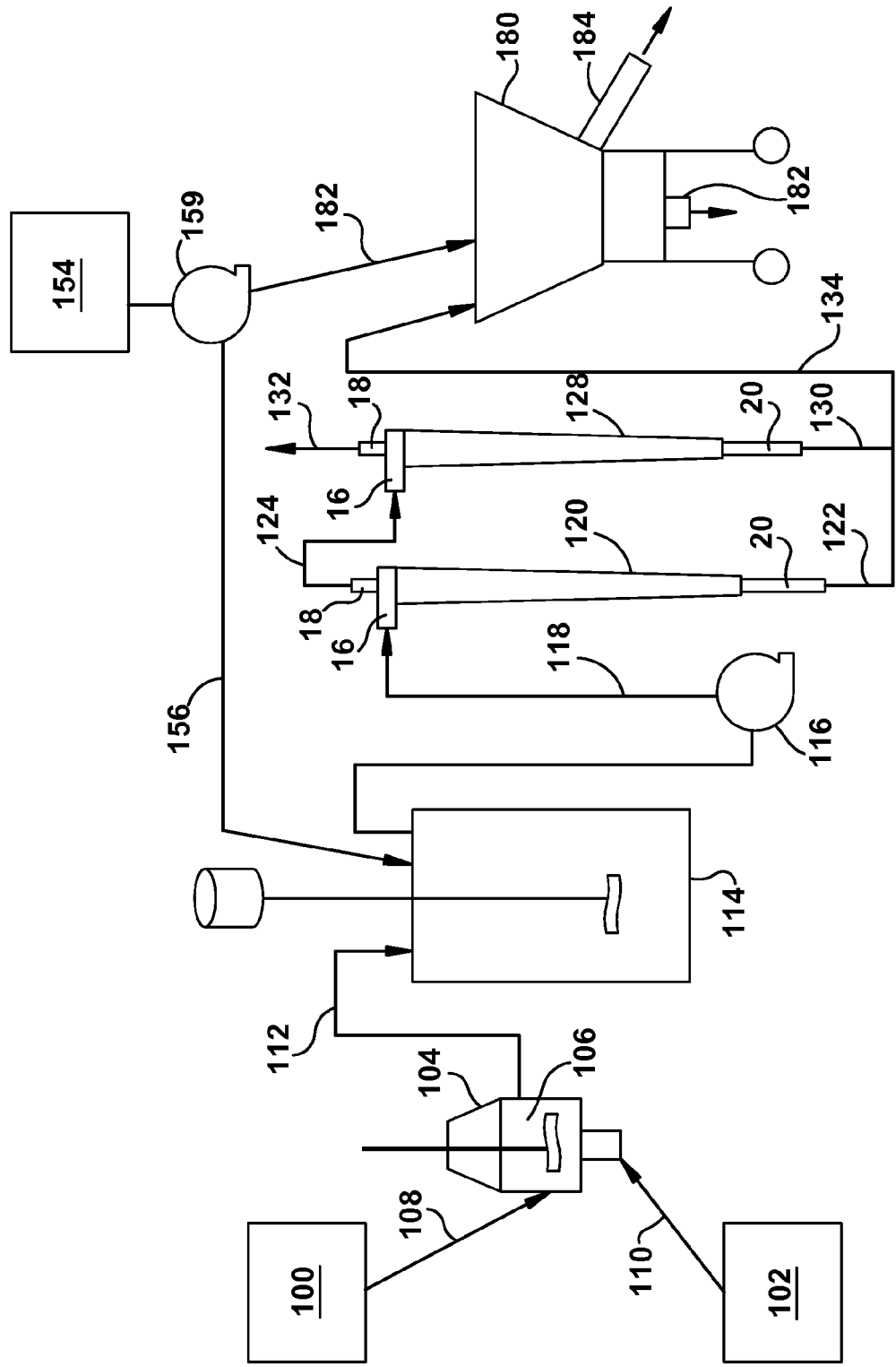
FIG. 4 is a flow diagram of an improved pharmaceutical production process with the hydrocyclone in use along with dead-end filtration to remove CP, washing microspheres, and drying to obtain sustained release microspheres. Drying is typically conducted by blowing a stream of air or nitrogen.

FIG. 4 is a similar process to FIG. 3, except it uses a wet sieve apparatus 180 instead of hollow fiber filter (HFF) to process the microspheres and does not include the SRV. Similar parts have similar reference numerals throughout the several views of this disclosure. Tubing 134 from the underflow outlets 20 of the first and second hydrocyclones 120, 128 leads to the wet sieve 180. The underflow streams 122, 130 from the first and second hydrocyclones 120, 128 are combined and travel along the tubing 134 to the wet sieve. Wash water from source 154 can be pumped by pump 159 into the sieve unit and water will be drained through port 182. Microspheres can be dispensed as a slurry through 184. Also, the microspheres in the sieve unit could be dried in the sieve itself by flowing dry air or inert gas at appropriate temperature and the dried microsphere could be collected as a bulk powder through port 184. SWECO sieve units operate under a parameter (unique vibration pattern) that allows the dry particles (or slurry) to discharge efficiently.

Evaluation of the Hydrocyclone for Formation of Sustained Release Microspheres

The efficiency of hydrocyclone operation can be determined by the concentration coefficient and yield of microspheres through the underflow. Concentration coefficient is the ratio of particle concentration in the underflow to the feed suspension. A higher concentration coefficient means effective separation of particles from the continuous phase. A higher inlet flow of suspension will result in a higher inlet pressure in the hydrocyclone. A higher inlet pressure provides a higher concentration coefficient. For microsphere manufacturing a higher concentration coefficient of particles is relevant. A flow rate ratio between underflow and overflow is a factor that should be considered along with efficient separation. If the underflow is low it is beneficial for the process since relatively large amounts of water can be removed from the system quickly through the overflow. However, there is a possibility of losing a fraction of particles in the overflow. Appropriate hydrocyclone type, and its manufactured apex and inlet flow should be selected for good yield of particles along with efficient removal of water from the system. Yield of microspheres through the underflow should also be considered, especially while processing expensive pharmaceutical formulations. Yield is the ratio between the amount of microspheres obtained through the underflow outlet compared to the amount through the inlet. The amount of microspheres is a combination of concentration of microspheres and flow rate of the suspension. If necessary, multiple hydrocyclones in series can be used to improve yield and to achieve a desired yield.

Removal of smaller particles occurs through the overflow. The range of particle size of small particles to be removed is based on the type of hydrocyclone, and its manufactured apex and flow rate.

EXAMPLE 1

Processing Microsphere Suspension Using a Hydrocyclone: Effect of Inlet Flow Rate, Apex ID and Particle Concentration on Concentration Coefficient and Particle Size A microsphere suspension was prepared from a polylactide-co-glycolide solution in dichloromethane by an oil-in-water process using an in-line Silverson mixer as per U.S. Pat. No. 5,945,126. Polyvinyl alcohol solution (0.35%) was used as the continuous phase. The Silverson mixing speed was 7000 rpm. Microparticles were washed to remove residual solvents and the particles were finally suspended in water. The concentration of microspheres in the suspension was 49 mg/g. Subsequently, suspensions having lower concentrations as shown in Table 1 were also prepared by diluting it further in water. The suspension was maintained in a 20 L Applikon vessel (intermediate vessel, IMV) during the study and continuously stirred to maintain homogeneity. Suspension samples from the IMV were taken for concentration and particle size analysis before hydrocyclone processing.

The suspension was pumped using a peristaltic pump at the flow rates shown in Table 1 into the inlet port of the hydrocyclone. Hydrocyclone Type GMAX1U-3125 having Apex 118 received from Krebs Engineers was used. The suspension from a 20 L Applikon (IMV) was pumped to the hydrocyclone inlet and samples were obtained from two outlets; the bottom outlet which produced the underflow retainent stream and top outlet which is the overflow. In these experiments, underflow was approximately 20% of the overflow, which varied slightly, however, based on the conditions.

Table 1 shows the results. As the flow rate increases the concentration of the microspheres in the retainant (underflow) increased. For the suspension having the particle concentration of 49 mg/g at the inlet flow rate of 10 L/min the concentration of the microspheres in the underflow stream was 2.5 times compared to the bulk suspension. Thus, by processing a 20 L suspension through the hydrocyclone approximately 50% of the particles were collected in approximately 2 L (20% of the volume) in 2 minutes duration. A higher inlet flow rate produced the underflow stream at even higher concentrations. Experiments using dilute suspension showed even higher concentration coefficients as shown in Table 1. Additionally, the particle size distribution (volume distribution) showed that the underflow stream contained less smaller particles since smaller particles were removed through the overflow stream. Particle size at 10% volume distribution showed up to 100% increase. Thus, particle size showed a considerable reduction of smaller particles from the system.

TABLE 1

Effect of Particle Concentration and Flow Rate on Concentration Coefficient and Particle Size

| Conc. of Microspheres in IMV (g/g) | Inlet flow rate (L/min) | Inlet pressure (PSI) | Conc. of particles in underflow (g/g) | Conc. ratio in underflow versus in IMV (inlet flow) | 10% Cumulative Volume Fraction (10% CVF) | | 50% Cumulative Volume Fraction (50% CVF) | |
|---|---|---|---|---|---|---|---|---|
| | | | | | Micron Size | % Change compared to bulk (IMV) | Micron Size | % Change compared to bulk (IMV) |
| 0.049 | | | Bulk sample from IMV | | 3.96 | N/A | 26.9 | N/A |
| | 10.0 | 10 | 0.124 | 2.5 | 5.87 | +48 | 30.0 | +12 |
| | 12.8 | 14 | 0.154 | 3.1 | 6.57 | +66 | 30.0 | +12 |
| | 14.3 | 16 | 0.169 | 3.5 | 6.44 | +63 | 29.7 | +10 |
| 0.025 | | | Bulk Sample from IMV | | 3.07 | N/A | 24.2 | N/A |
| | 10.0 | 8 | 0.074 | 3.0 | 5.82 | +90 | 28.6 | +18 |
| | 12.8 | 13 | 0.089 | 3.6 | 6.16 | +101 | 28.4 | +17 |
| | 14.3 | 16 | 0.095 | 3.8 | 6.31 | +106 | 27.7 | +14 |
| 0.006 | | | Bulk Sample from IMV | | 3.22 | N/A | 24.9 | N/A |
| | 10.0 | 7 | 0.017 | 2.8 | 5.85 | +82 | 28.3 | +14 |
| | 12.8 | 12 | 0.020 | 3.3 | 6.45 | +100 | 28.5 | +15 |
| | 14.3 | 14 | 0.022 | 3.7 | 6.24 | +94 | 27.8 | +11 |

EXAMPLE 2

The effect of the apex ID of the hydrocyclone on concentration coefficient and particle size of microspheres was evaluated using hydrocyclone model GMAX1U-3125 (from Krebs) using three different apex IDs A (0.118), B (0.157), and C (0.197) from Krebs Studies were performed using the microsphere suspension having 15 mg/g particle concentration at two different flow rates, 8.7 L/min and 12.6 L/min. When the hydrocyclone apex was changed from A to C, the concentration coefficient increased from 4.0 to 5.0 at 8.7 L/min flow rate and from 4.9 to 6.7 at 12.6 L/min flow rate. Additionally, apex C removed a substantial amount of small particles. In the bulk suspension (feed) 10% of the particles were under 2.76 micron. Upon processing through the hydrocyclone the underflow showed 10% of the particles were under 13 microns in particle size. By selecting appropriate apex and inlet flow rate smaller particles could be eliminated to various extents from the product.

TABLE 2

Effect of Apex type on Concentration Coefficient and Particle Size

| Apex | Inlet Flow (L/min) | Conc. of particles in underflow (g/g) | Conc. ratio in underflow versus in IMV | 10% particles under | | 50% particles under | |
|---|---|---|---|---|---|---|---|
| | | | | Micron Size | % Change compared to bulk (IMV) | Micron Size | % Change compared to bulk (IMV) |
| Bulk Sample from IMV (Conc. 0.015 g/g) | | | | 2.76 | N/A | 27.1 | N/A |
| A | 8.7 | 0.060 | 4.0 | 7.41 | 168 | 38.2 | 41 |
| | 12.6 | 0.074 | 4.9 | 7.83 | 184 | 36.3 | 34 |
| B | 8.7 | 0.060 | 4.0 | 7.95 | 188 | 39.2 | 45 |
| | 12.6 | 0.080 | 5.3 | 9.17 | 232 | 38.1 | 41 |
| C | 8.7 | 0.075 | 5.0 | 10.6 | 284 | 41.1 | 52 |
| | 12.6 | 0.100 | 6.7 | 13.0 | 371 | 40.5 | 49 |

EXAMPLE 3

Doxycycline Microspheres Processed by Hollow Fiber Filter and Hydrocyclone

Doxycycline is an antibiotic that requires sustained drug level in the blood for efficacy. Doxycycline microspheres for two week release were prepared by processing the microspheres using a hollow fiber filter (HFF) process. Using the HFF process, the suspension produced by the in-line Silverson was approximately 50 L and took approximately 50 minutes to eliminate 30 L water. Using the hydrocyclone it took only 4 minutes to eliminate 30 L water. Also, the microspheres processed through the hollow fiber filter contained smaller particles. For this product, the drug release kinetics performed by in-vitro and in-vivo (rat model) showed an initial burst. Microspheres processed through the hydrocyclone were found to be substantially free from small particles, which eliminated low drug containing small particles. The resultant microspheres showed considerably lower initial burst and higher drug load. The following procedure provides details.

Microsphere Preparation:

Doxycycline containing poly(d,l-lactide-co-glycolide) (PLGA) microspheres were prepared using doxycycline hyclate from Hovione and PLGA (RG503H) from Boehringer Ingelheim by an oil-in-water process. The dispersed phase (organic phase) was prepared by dissolving 20 g doxycycline hyclate, 80 g RG503H (PLGA), 240 g methylene chloride and 60 g methanol. The solution was then filtered using a 0.2 micron PTFE (Satafluor 150 from Sartorious) filter. The continuous phase (aqueous phase) was 0.5% polyvinyl alcohol (PVA) in water prepared by dissolving 300 g low molecular weight PVA in hot water (70 to 90° C.). The solution was then cooled to ambient temperature and water was added to reach 60 L in total volume. The continuous phase was also filtered through 0.2 micron PVDF (Opticap XL10 from Millipore). Doxycycline microspheres were prepared using an in-line mixer as described in U.S. Pat. No. 5,945,126 at a CP flow rate of 4 L/min and a DP flow rate of 30 mL/min. The Silverson stirring speed was 5000 rpm. A microsphere suspension produced at a rate of approximately 4 L/min was collected in a 100 L tank and the suspension in the intermediate vessel (IMV) was stirred for suspension homogeneity.

Concentrating Suspension by Hollow Fiber Filter:

SRV (3 L bioreactor from Applikon) equipped with inlet tubes for suspension, water and diluent and also a re-circulation line through a Type 5A hollow fiber filter (HFF from GE Healthcare) was used for processing the suspension. The suspension was pumped from an intermediate vessel IMV at 600 mL/min. The suspension in the SRV was re-circulated through the HFF at 6 L/min and permeate was removed at 600 mL/min. Thus, to remove 30 L water, it took approximately 50 minutes. To process the entire suspension in the IMV, it took approximately 80 minutes. A suspension volume of 1.5 L was maintained in the SRV and the entire suspension was condensed into the 1.5 L volume.

Concentrating Suspension by Hydrocyclone:

Three hydrocyclones, Type GMAX1U-3125 having apex IDs 0.197 (HC-1), 0.197 (HC-2), and 0.118 (HC-3) were connected in series. The outlet from the IMV was connected to the inlet of HC-1. Underflow from HC-1 was collected in a pre-weighed glass container. Overflow from HC-1 was connected to the inlet of HC-2. Underflow from HC-2 was also collected in a pre-weighed glass container. Overflow from HC-2 was connected to the inlet of the HC-3. Underflow from HC-3 was collected in a pre-weighed glass container. Overflow from HC-3 was a waste stream; however it was collected for particle size and particle concentration measurement. Samples from individual containers including IMV were removed for analytical purposes. A suspension from the IMV was pumped at 13 L/min to the inlet of HC-1 using a peristaltic pump (Watson Marlow). Under flow and overflow were collected. The total volume of underflow from HC-1, HC-2 and HC-3 was approximately 19 L. This was further transferred to the solvent removal vessel (SRV) using a peristaltic pump, processed using a hollow fiber filter eliminating CP at 600 mL/min condensing the microspheres in 1.5 L volume.

Washing of Microspheres:

After concentrating the microspheres from 50 L volume to 1.5 L volume using the HFF or Hydrocyclone-HFF combination, the microspheres were washed as a suspension with room temperature water for 10 minutes, 35° C. water for 40 minutes (20 minutes at temperature and a 20 minute ramp time) and again with room temperature water for approximately 30 minutes. This was performed by volume exchanges as described in U.S. Pat. No. 6,270,802.

Recovery and Freeze Drying:

Washed microspheres were recovered on a PVDF membrane using dead end filtration and freeze dried. Freeze drying was performed by freezing it to −35° C. over 1 hours and holding it at −35° C. for 3 hours, increasing the temperature from −35 to −5° C. over 2 hours (≤150 mT vacuum), −5 to +5° C. over 6 hours (≤150 mT vacuum) and +5 to +30° C. over 2 hours (≤150 mT vacuum) and holding it at +30° C. for 8 hours (≤150 mT vacuum).

Microspheres prepared by the HFF process and by the hydrocyclone process were characterized for drug content, particle size distribution and drug release. Microspheres prepared by the HFF process were evaluated for in-vivo drug release in rats. For the hydrocyclone process, drug load and particle size were measured for individual fractions also for information purposes. Additionally, particle concentrations in various suspensions were also determined to evaluate the hydrocyclone efficiency comparison.

Table 3 shows the performance of the hydrocyclone process. As shown, the HC processed the suspension at approximately 13 L/min while the HFF processed the suspension at 600 mL/min only. The hydrocyclone enables processing relatively large volumes in a shorter duration compared to the HFF due to the reasons previously described. A microsphere suspension could be processed at the same rate of production using a HC and a large holding vessel is not required. Hence, smaller process equipments could be used. For example, if the microsphere suspension production rate is 15 L/min, the HC could easily remove CP at 15 L/min. The equipment is very compact (approx. 1 ft long 1 inch dia). However, to eliminate the CP at 15 L/min through HFF, there is no HFF available that operates at this rate, therefore 2 or 3 HFF would be placed in parallel and the re-circulation rate of the suspension through the HFF has to be 150 L/min. This requires a large pump. Therefore, the equipment is large and cumbersome.

TABLE 3

Flow Rate, Concentration of Microspheres and Particle Size Distribution

| | | HC-1 | HC-2 | HC-3 |
|---|---|---|---|---|
| Flow rate (L/min) | Inlet flow | 13.0 | 11.79 | 10.99 |
| | Underflow | 1.81 | 0.80 | 0.84 |
| | Overflow | 11.79 | 10.99 | 10.15 |
| Particle concentration (g/g) | Inlet | 0.00185 | 0.00065* | 0.00048* |
| | Underflow | 0.00906 | 0.00175 | 0.00119 |
| | Overflow | 0.00065* | 0.00048* | 0.0004* |
| Particle Size for Inlet flow | 10% Under | 4.98 | | |
| | 25% Under | 12.0 | | |
| | 50% Under | 30.2 | | |
| | 75% Under | 46.1 | | |
| | 90% Under | 59.7 | | |
| Particle size for Underflow | 10% Under | 10.7 | 4.45 | 4.20 |
| | 25% Under | 30.3 | 11.7 | 9.03 |
| | 50% Under | 44.6 | 28.8 | 24.6 |
| | 75% Under | 57.3 | 42.3 | 37.7 |
| | 90% Under | 68.3 | 53.8 | 48.4 |
| Particle size for overflow | 10% Under | | | 3.39 |
| | 25% Under | | | 5.94 |
| | 50% Under | | | 11.3 |
| | 75% Under | | | 23.6 |
| | 90% Under | | | 32.9 |

*Calculated

The results show that the concentration of doxycycline microspheres in the underflow of the first HC was approximately 5 times that of the inlet and 14 times that of the overflow. Out of 96 g microspheres processed from the 50 L suspension, 66 g of microspheres were collected in a 7.2 L suspension in the HC-1 underflow. Thus, 69% of the doxycycline microspheres were collected in 17% of the volume and these particles are substantially free from smaller particles. This was achieved rapidly within 4 minutes of processing.

The concentration of microspheres in the underflow of the second HC was 2.7 times the particle concentration of the inlet and 3.7 times compared to the overflow. The results show that 8.2 g (9% of bulk) were recovered though the HC-2 underflow in 4.7 L volume. Thus 9% of microspheres in the original bulk (in IMV) were collected in 9% volume. Concentration of the microspheres in the underflow of HC-2 is similar to that of the original suspension in the IMV. Even though there is no net gain on particle concentration, this fraction could be collected for good yield, if needed.

Concentration of microspheres in the underflow of the HC-3 was 2.4 times the concentration of the particles in the overflow. Concentration of the particles in the underflow is even lower, lower than that of the bulk suspension in the IMV. Again, this fraction could be included in the product, if yield of the particles is critical. The concentration of particles in the underflow decreases with added HC in series because the concentration of particles entering into the subsequent HC is lower and lower compared to the concentration in the IMV. Multiple HC are introduced here for the purpose of good yield only.

Figure 5A:
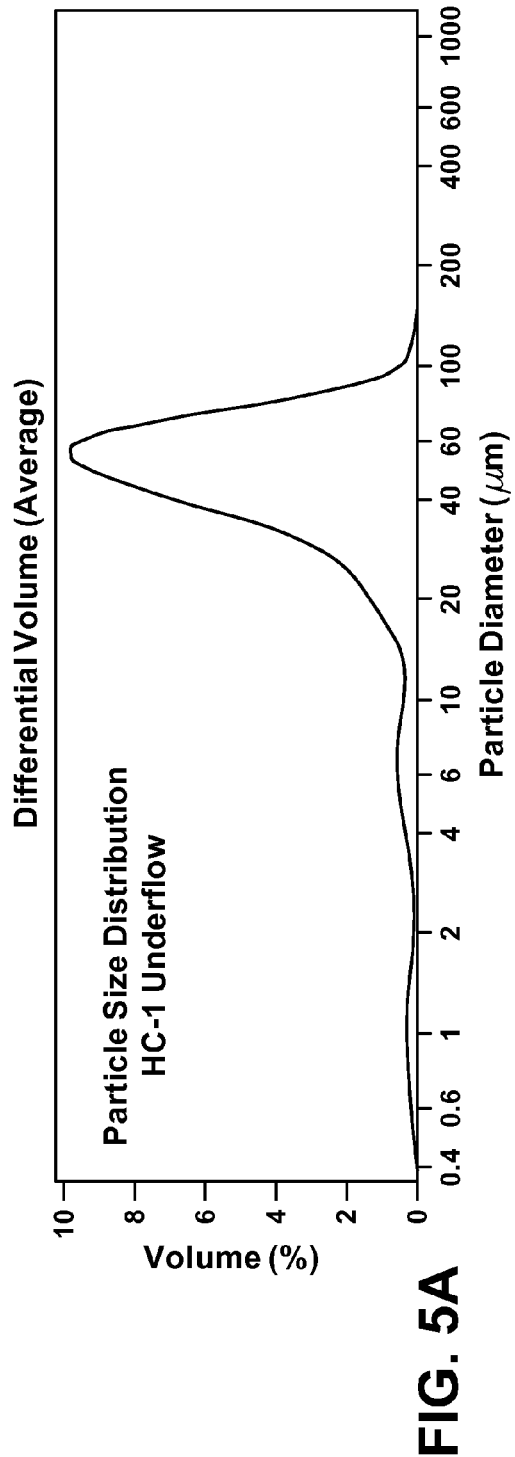
FIG. 5A is a particle size distribution curve for a hydrocyclone 1 (HC-1) underflow fraction and this is compared in FIG. 5B to the particle size distribution curve for a hydrocyclone 3 (HC-3) overflow fraction while processing doxycycline microspheres using hydrocyclones.
Figure 5B:
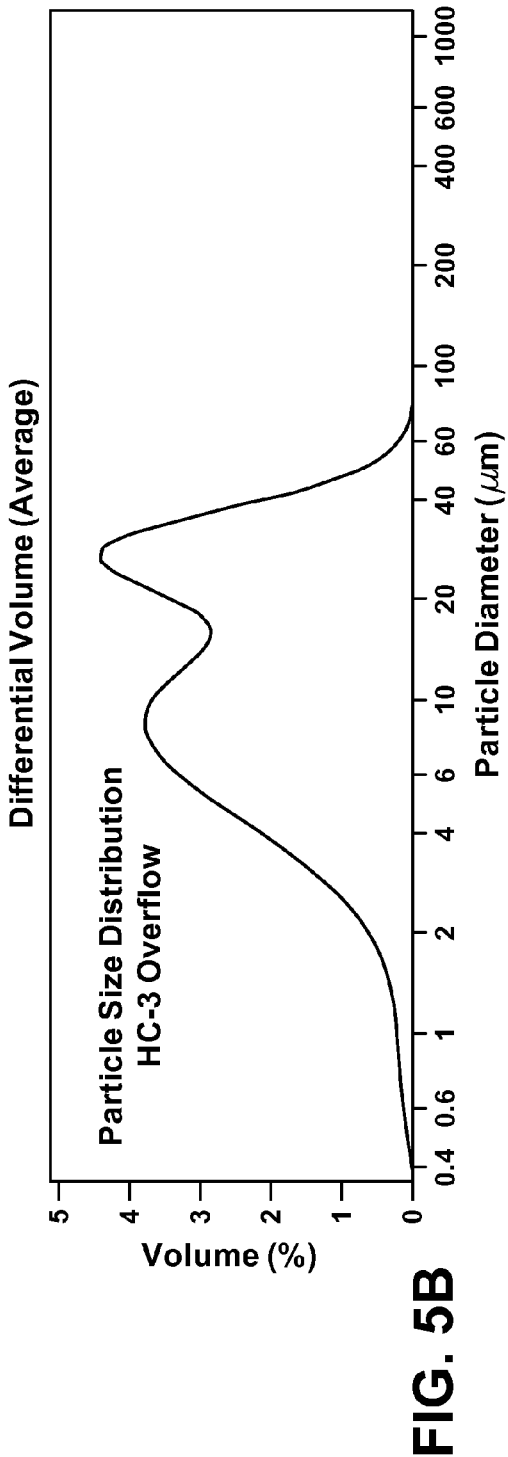
Figure 6:
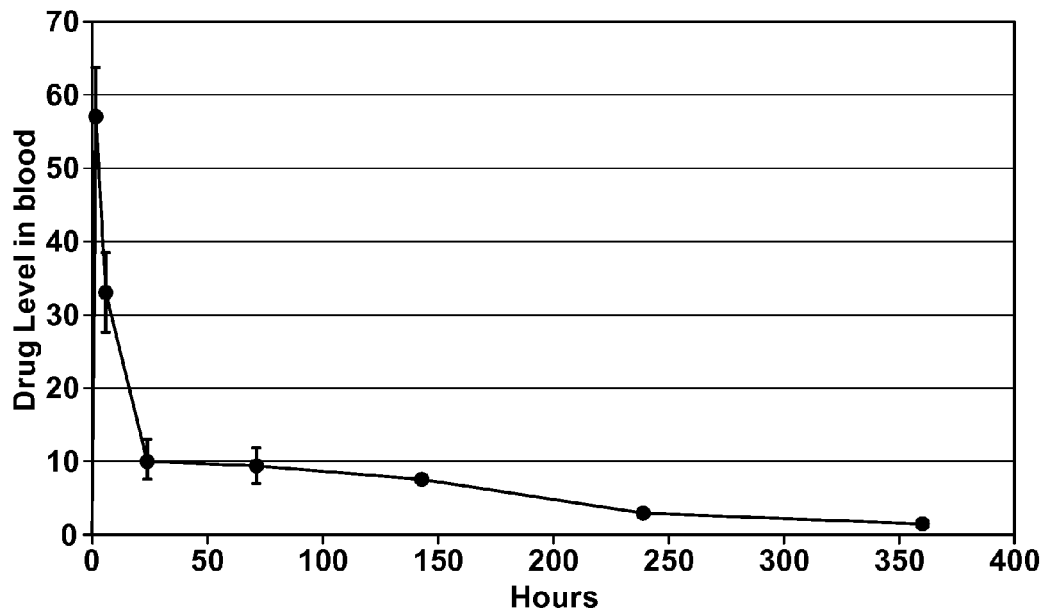
FIG. 6 is a doxycycline level in rat blood while injecting doxycycline microspheres processed by a hollow fiber filter (HFF) alone at the dose of 10 mg drug/Kg rat.
Figure 7:
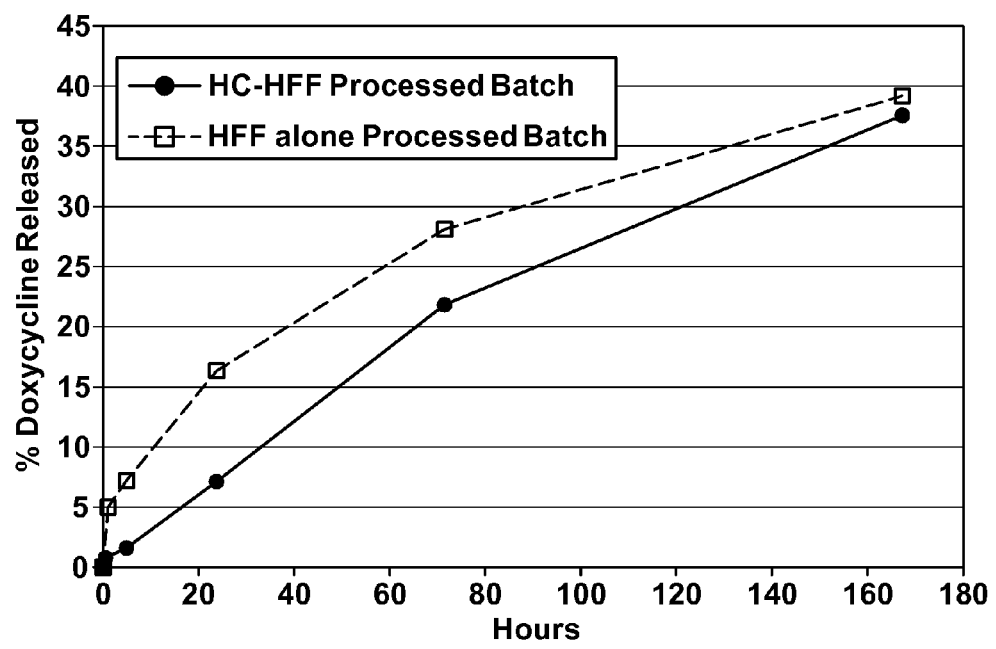
FIG. 7 is an in-vitro release comparison of doxycycline microspheres processed by a hydrocyclone and hollow fiber filter (HC-HFF) versus a hollow fiber filter (HFF) alone performed under physiological conditions (PBS, 37° C.).

Particle size also showed a large difference among the portions received at the HC underflow and overflow. Microspheres received through HC-1 underflow had a small amount of small particles (FIG. 5A) and the HC-3 overflow contained a majority of the smaller particles (FIG. 5B).

For the doxycycline microsphere run, underflow from all three HCs were delivered to the SRV and further processed (concentrated and washed) using the HFF. Resulting microspheres were compared with the microspheres prepared by HFF filter alone for drug load, particle size and drug release properties. Since HC-2 and HC-3 underflow were also combined with the product there were some smaller particles in the HC processed microspheres; however, the amount of smaller particles is much less compared to the HFF alone processed microsphere batch. Drug load in the microspheres was 12.3% for the HC-HFF processed microspheres. HFF-alone processed microspheres showed only a 9.4% drug load. This was primarily due to the presence of smaller particles having low drug load. It was found that the particles in the overflow of HC-3 had only 4.3% drug load. Lower drug load microspheres are not preferred since it requires more microspheres to be injected to provide a similar dose.

An additional benefit found in the HC-HFF processed microspheres was the reduction of initial burst release. HFF-alone processed microspheres were injected in rats to follow the in-vivo release rate. Six rats were injected with the HFF processed microspheres at the dose of 10 mg doxycycline/Kg rat. Five rats were used for the test group. Blood samples were taken at 2 hours, 6 hours, 1 day, 3 days, 6 days, 10 days, 15 days and 21 days and the concentration of doxycycline in the blood was assayed by HPLC-MS. Results showed that HFF-alone processed microspheres had a huge initial burst (FIG. 6). These microspheres were prepared to have approximately 10 days release duration. Low to moderate burst is desirable from these formulations. The higher burst shown in FIG. 6 is not desirable.

HFF-alone processed microspheres and HC-HFF processed microspheres were tested for in-vitro release under physiological conditions. This was performed with 20 mg microspheres in 20 mL phosphate buffered saline contained in a 40 mL screw capped tubes placed in a 37° C. shaking water bath. The entire supernatant was removed for assay at each sampling points, 1 hour, 5 hours, 1 day, 3 days and 7 days and replaced with fresh release media. Drug concentration in the supernatant was assayed for doxycycline by UV spectrophotometer against calibration standards. Percentage of drug released at each time point was calculated from the total drug introduced into the sample tube compared to that found in the release media. The results are shown in FIG. 7 as a plot for cumulative release against time. It was found that HC-HFF processed microspheres have much lower initial burst (one-fifth) compared to the HFF alone processed microspheres. Thus, by eliminating smaller particles that had low drug load and faster release, unwanted initial burst release was reduced from the microspheres. The HC-HFF processed microspheres showed steady state nearly zero-order release while the HFF alone processed microspheres showed five times higher initial burst and higher initial release during the initial five days.

Many modifications and variations of the invention will be apparent to those of ordinary skill in the art in light of the foregoing disclosure. Therefore, it is to be understood that, within the scope of the appended claims, the invention can be practiced otherwise than has been specifically shown and described.

What is claimed is:

1. A system for processing microspheres comprising:

a vessel containing a suspension of solidified microspheres in a suspending medium comprising a solvent;

a hydrocyclone (HC-1) having a fluid inlet, a first fluid outlet and a second fluid outlet, wherein said fluid inlet is in fluid communication with said vessel and receives said suspension, said second fluid outlet discharges a flow (flow A) of said suspension having an increased concentration of said microspheres relative to said suspension in said vessel, and said first fluid outlet discharges a flow (flow B) of said suspending medium having a lower concentration of said microspheres relative to said suspension in said vessel; and, a hollow fiber filter or a wet sieve having an inlet in fluid communication with said second fluid outlet, said system further comprising a second hydrocyclone (HC-2) having a fluid inlet, a first fluid outlet and a second fluid outlet, wherein said fluid inlet is in fluid communication with said first fluid outlet of hydrocyclone HC-1, said HC-2 second fluid outlet discharges a flow (flow C) of said suspension having an increased concentration of said microspheres relative to said flow B discharged from said first fluid outlet of hydrocyclone HC-1, and wherein said system combines said flow A from said HC-1 second fluid outlet and said flow C from said HC-2 second fluid outlet for fluid communication to said inlet of said hollow fiber filter or said wet sieve.

2. The system of claim 1, further comprising a solvent removal vessel (SRV) interposed between and in fluid communication with said inlet of said wet sieve or said hollow fiber filter and said second fluid outlets of said HC-1 and said HC-2, said SRV capable of receiving and washing said microspheres in said suspension discharged and combined from said second outlets of said HC-1 and said HC-2 to remove said solvent from said suspension.

3. The system of claim 2, said system comprising a hollow fiber filter having an inlet for receiving said suspension from said SRV, and an outlet in fluid communication with an inlet in said SRV, said system capable of recirculating said suspension from said SRV, through said hollow fiber filter and back to said SRV.

4. The system of claim 1, said HC-1 having an apex I.D. and an inlet flow rate that increases the 10% cumulative volume fraction (CVF) of said microspheres in said flow A of said suspension from said second fluid outlet relative to a 10% CVF of said microspheres in said suspension entering said HC-1.

5. The system of claim 1, said HC-1 having an apex I.D. and an inlet flow rate that increases the 10% cumulative volume fraction (CVF) of said microspheres in said flow A of said suspension from said second fluid outlet by at least 48% relative to a 10% CVF of said microspheres in said suspension entering said HC-1.

6. The system of claim 1, said HC-1 having an apex I.D. and an inlet flow rate that increases the 10% cumulative volume fraction (CVF) of said microspheres in said flow A of said suspension from said second fluid outlet by at least 63% relative to a 10% CVF of said microspheres in said suspension entering said HC-1.

7. The system of claim 1, said HC-1 having an apex I.D. and an inlet flow rate that increases the 10% cumulative volume fraction (CVF) of said microspheres in said flow A of said suspension from said second fluid outlet by at least 82% relative to a 10% CVF of said microspheres in said suspension entering said HC-1.

8. A method for processing microspheres comprising:
forming a suspension of solidified microspheres in a suspending medium in a vessel;
moving said suspension from said vessel to a fluid inlet of a hydrocyclone (HC-1), said HC-1 further having a first fluid outlet and a second fluid outlet;
removing from said second fluid outlet a flow (flow A) of said suspension having an increased concentration of said microspheres relative to said suspension in said vessel;
removing from said first fluid outlet a flow (flow B) of said suspension having a decreased concentration of microspheres relative to said suspension in said vessel; and,
moving said flow A from said second fluid outlet to an inlet of a hollow fiber filter or wet sieve,
and further comprising selecting one or both of an apex I.D. and an inlet flow rate of said HC-1 such that a 10% cumulative volume fraction (CVF) of said microspheres in said flow A from said second fluid outlet is increased relative to a 10% CVF of said microspheres in said suspension entering said HC-1 from said vessel.

9. The method of claim 8 comprising moving said suspension from said second fluid outlet to an inlet of said hollow fiber filter.

10. The method of claim 8 comprising moving said suspension from said second fluid outlet to an inlet of said wet sieve.

11. The method of claim 8, further comprising moving said flow B from said first fluid outlet of HC-1 to a fluid inlet of a second hydrocyclone (HC-2), having a first fluid outlet and a second fluid outlet;
removing from said second fluid outlet of said HC-2 a flow (flow C) of said suspension having an higher concentration of said microspheres relative to said flow B discharged from said first fluid outlet of HC-1;
removing from said first fluid outlet of HC-2 a flow (flow D) of said suspension having a lower concentration of microspheres relative to said flow C discharged from said second outlet of HC-2; and,
combining and moving said flows A and C from said second fluid outlets of said HC-1 and said HC-2 to said inlet of said hollow fiber filter or said wet sieve.

12. The method of claim 11, further comprising moving said suspension from said second fluid outlets of said HC-1 and said HC-2 to a fluid inlet of a solvent removal vessel (SRV) capable of receiving and washing said microspheres in said suspension, and moving said combined flows A and C from an outlet of said SRV to said inlet of said hollow fiber filter or said wet sieve.

13. The method of claim 12, further comprising moving said combined flows A and C from said outlet of said SRV to said inlet of a hollow fiber filter; and moving said combined flows A and C from an outlet of said hollow fiber filter to said inlet of said SRV.

14. The method of claim 11, further comprising selecting one or both of an apex I.D. and an inlet flow rate of said HC-1 and HC-2 such that a 10% cumulative volume fraction (CVF) of said microspheres in said flow C from said second fluid outlet of said HC-2 is increased by at least 48% relative to a 10% CVF of said microspheres in said suspension entering said hydrocyclone HC-1 from said vessel.

15. The method of claim 8, further comprising moving said flow A from said second fluid outlet of said HC-1 to a fluid inlet of a solvent removal vessel (SRV) capable of receiving and washing said microspheres in said suspension, and moving said suspension from an outlet of said SRV to said inlet of said hollow fiber filter or said wet sieve.

16. The method of claim 15, further comprising moving said flow A from said second fluid outlet of said HC-1 to said fluid inlet of said SRV; moving said flow A from said outlet of said SRV to an inlet of a hollow fiber filter; and moving said flow A from an outlet of said hollow fiber filter to said inlet of said SRV.

17. The method of claim 8, comprising selecting one or both of an apex I.D. and an inlet flow rate of said HC-1 such that a 10% cumulative volume fraction (CVF) of said microspheres in said flow A from said second fluid outlet is increased by at least 48% relative to a 10% CVF of said microspheres in said suspension entering said HC-1 from said vessel.

18. The method of claim 8, comprising selecting one or both of an apex I.D. and an inlet flow rate of said HC-1 such that a 10% cumulative volume fraction (CVF) of said microspheres in said flow A from said second fluid outlet is increased by at least 63% relative to a 10% CVF of said microspheres in said suspension entering said HC-1 from said vessel.

19. The method of claim 8, comprising selecting one or both of an apex I.D. and an inlet flow rate of said HC-1 such that a 10% cumulative volume fraction (CVF) of said microspheres in said flow A from said second fluid outlet is increased by at least 82% relative to a 10% CVF of said microspheres in said suspension entering said HC-1 from said vessel.

* * * * *